(12) United States Patent
Lee et al.

(10) Patent No.: US 12,404,252 B2
(45) Date of Patent: *Sep. 2, 2025

(54) SALT OF 2-AMINO-2-(2-(1-DECYL-1H-1,2,3-TRIAZOL-4-YL)ETHYL)PROPANE-1,3-DIOL, AND PHARMACEUTICAL COMPOSITION CONTAINING SAME

(71) Applicant: NEXTGEN BIOSCIENCE CO., LTD, Seongnam-si (KR)

(72) Inventors: Bongyong Lee, Seoul (KR); Yanghae Park, Seoul (KR); Eunjeong Kim, Seongnam-si (KR)

(73) Assignee: NEXTGEN BIOSCIENCE CO., LTD, Gyeonggi-Do (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/688,333

(22) PCT Filed: Nov. 4, 2022

(86) PCT No.: PCT/KR2022/017235
§ 371 (c)(1),
(2) Date: Feb. 29, 2024

(87) PCT Pub. No.: WO2023/080708
PCT Pub. Date: May 11, 2023

(65) Prior Publication Data
US 2024/0336578 A1 Oct. 10, 2024

(30) Foreign Application Priority Data
Nov. 4, 2021 (KR) ........................ 10-2021-0150651

(51) Int. Cl.
*C07D 249/04* (2006.01)
*A61K 31/4192* (2006.01)
*A61P 1/00* (2006.01)
*A61P 17/14* (2006.01)

(52) U.S. Cl.
CPC ........ *C07D 249/04* (2013.01); *A61K 31/4192* (2013.01); *A61P 1/00* (2018.01); *A61P 17/14* (2018.01)

(58) Field of Classification Search
CPC .......... C07D 249/04; A61P 17/14; A61P 1/00; A61K 31/4192
See application file for complete search history.

(56) References Cited

U.S. PATENT DOCUMENTS

2012/0129813 A1  5/2012  Heidelbaugh et al.
2016/0340321 A1  11/2016  Hou et al.

FOREIGN PATENT DOCUMENTS

| KR | 20170087813 A | 7/2017 |
| KR | 20180036318 A | 4/2018 |
| KR | 20200087717 A | 7/2020 |
| RU | 2654483 C2 | 5/2018 |
| WO | 2020172714 A1 | 9/2020 |

OTHER PUBLICATIONS

Danese et al. Targeting S1P in Inflammatory Bowel Disease: New Avenues for Modulating Intestinal Leukocyte Migration, Journal of Crohn's and Colitis, 2018, S678-S686 (Year: 2018).*

Kiuchi, M. et al., "Synthesis and immunosuppressive activity of 2-substituted 2-aminopropane-1,3-diols and 2-aminoethanols," Journal of Medicine Chemistry, vol. 43, No. 15, Jul. 27, 2000.

ISA Korean Intellectual Property Office, International Search Report Issued in Application No. PCT/KR2022/017235, Feb. 10, 2023, WIPO, 6 pages.

* cited by examiner

*Primary Examiner* — Adam C Milligan
*Assistant Examiner* — William Y Lee
(74) *Attorney, Agent, or Firm* — McCoy Russell LLP

(57) ABSTRACT

The present invention relates to a novel salt of 2-amino-2-(2-(1-decyl-1H-1,2,3-triazol-4-yl)ethyl)propane-1,3-diol, and a pharmaceutical composition containing same. In the results of a comparison with hydrochloride salt of 2-amino-2-(2-(1-decyl-1H-1,2,3-triazol-4-yl)ethyl)propane-1,3-diol and the other salts thereof, the novel salt of 2-amino-2-(2-(1-decyl-1H-1,2,3-triazol-4-yl)ethyl)propane-1,3-diol, according to the present invention, exhibits excellent effects in all of low hygroscopicity, standard stock solution stability, photostability, oxidation stability, pH-dependent stability, solubility and the like. The pharmaceutical composition, of the present invention, containing the novel salt as an active ingredient, can be effectively used for preventing or treating multiple sclerosis, ischemic stroke, focal segmental glomerulosclerosis (FSGS), inflammatory bowel disease, interstitial fibrosis and tubular atrophy (IFTA) or alopecia areata (AA).

8 Claims, 15 Drawing Sheets

FIG. 6

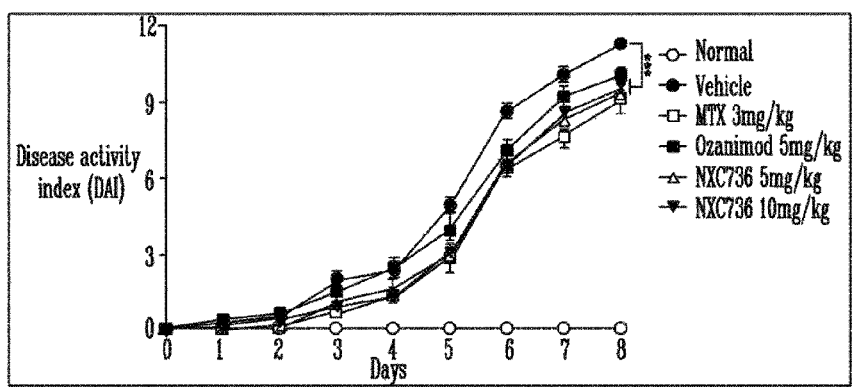

Disease activity index (DAI) of DSS-induced colitis mice.
The mice were grouped with Normal, 2.5% DSS + Vehicle,
2.5% DSS + MTX (3 mg/kg; IP; TIW), 2.5% DSS + Ozanimod (5 mg/kg; PO; QD),
2.5% DSS + NXC736 (5 mg/kg; PO; QD), 2.5% DSS + NXC736 (10 mg/kg; PO; QD),
Data are expressed as the mean ± SEM.
* = $p < 0.05$,  = $p < 0.01$, and * = $p < 0.001$ versus Vehicle control

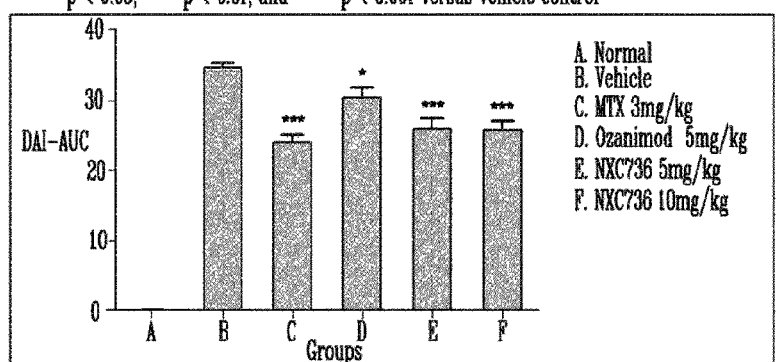

Area under the curve (AUC) of disease activity index in
DSS-induced colitis mice. The mice were grouped with Normal,
2.5% DSS + Vehicle, 2.5% DSS + MTX (3 mg/kg; IP; TIW),
2.5% DSS + Ozanimod (5 mg/kg; PO; QD), 2.5% DSS + NXC736 (5 mg/kg; PO; QD),
2.5% DSS + NXC736 (10 mg/kg; PO; QD), Data are expressed as
the mean ± SEM. * = $p < 0.05$,  = $p < 0.01$, and * = $p < 0.001$ versus Vehicle control.

FIG. 7

| Group / Concentration (μM) | | $I_{initial}$ (pA) | $I_{drug}$ (pA) | $I_{rel}$ | Suppression rate (%) | Compensated suppression rate (%) | $IC_{50}$ (μM) | H |
|---|---|---|---|---|---|---|---|---|
| A | Mean | 1279 | 1238 | 0.9682 | 3.18 | 0.00 | 12.94 | 1.527 |
| 0 | S.D. | 50 | 37 | 0.0399 | 3.99 | 4.12 | | |
|   | N | 3 | 3 | 3 | 3 | 3 | | |
| B | Mean | 894 | 783 | 0.8720 | 12.80 | 9.94 | | |
| 1 | S.D. | 254 | 234 | 0.0190 | 1.90 | 1.96 | | |
|   | N | 3 | 3 | 3 | 3 | 3 | | |
| C | Mean | 1147 | 953 | 0.8328 | 16.72 | 13.98 | | |
| 3 | S.D. | 371 | 295 | 0.0434 | 4.34 | 4.48 | | |
|   | N | 3 | 3 | 3 | 3 | 3 | | |
| D | Mean | 1250 | 803 | 0.6291 | 37.09 | 35.03 | | |
| 10 | S.D. | 1085 | 722 | 0.1170 | 11.70 | 12.09 | | |
|   | N | 3 | 3 | 3 | 3 | 3 ** | | |
| E | Mean | 988 | 170 | 0.1683 | 83.17 | 82.62 | | |
| 30 | S.D. | 289 | 107 | 0.0707 | 7.07 | 7.31 | | |
|   | N | 3 | 3 | 3 | 3 | 3 ** | | |
| F | Mean | 1427 | 101 | 0.0712 | 92.88 | 92.64 | | |
| 0.1 | S.D. | 608 | 48 | 0.0160 | 1.60 | 1.66 | | |
|   | N | 5 | 5 | 5 | 5 | 5 ## | | |

A: Negative control group (External bath solution), B-E: Test substance group (NXC736), F: Positive control group (E-4031)
$I_{initial}$: Pre-treatment current
$I_{drug}$: Treatment current
$I_{rel}$: Relative current
S.D.: Standard deviation
N: Number of cells
$IC_{50}$: The half-maximal inhibitory concentration
H: Hill coefficient
**$p<0.01$ : Significantly different from the negative control group (A) by Dunnett's t-test.
$p<0.01$: Significantly different from the negative control group (A) by Student's t-test.

| NXC736 | Freebase | Hemifumarate | HCl |
|---|---|---|---|
| NXC736 Initial | | | |
| NXC736 60C75RH% 2W | | | |

Fig. 11

SALT OF 2-AMINO-2-(2-(1-DECYL-1H-1,2,3-TRIAZOL-4-YL)ETHYL)PROPANE-1,3-DIOL, AND PHARMACEUTICAL COMPOSITION CONTAINING SAME

CROSS REFERENCE TO RELATED APPLICATIONS

The present application is a U.S. National Phase of International Application No. PCT/KR2022/017235 entitled "NOVEL SALT OF 2-AMINO-2-(2-(1-DECYL-1H-1,2,3-TRIAZOL-4-YL)ETHYL)PROPANE-1,3-DIOL, AND PHARMACEUTICAL COMPOSITION CONTAINING SAME," and filed on Nov. 4, 2022. International Application No. PCT/KR2022/017235 claims priority to Republic of Korea Patent Application No. 10-2021-0150651 filed on Nov. 4, 2021. The present application also claims priority to Republic of Korea Application No. 10-2022-0145483 filed Nov. 3, 2022, which claims priority to Republic of Korea Patent Application No. 10-2021-0150651 filed on Nov. 4, 2021. The entire contents of each of the above-listed applications are hereby incorporated by reference for all purposes.

TECHNICAL FIELD

The present invention relates to a novel salt of 2-amino-2-(2-(1-decyl-1H-1,2,3-triazol-4-yl)ethyl) propane-1,3-diol and a pharmaceutical composition for novel uses containing the same. More specifically, the present invention relates to a fumarate salt or hemifumarate salt of 2-amino-2-(2-(1-decyl-1H-1,2,3-triazol-4-yl)ethyl) propane-1,3-diol and a pharmaceutical composition for novel uses containing the same.

BACKGROUND AND SUMMARY

2-Amino-2-(2-(1-decyl-1H-1,2,3-triazol-4-yl)ethyl) propane-1,3-diol compound (hereinafter referred to as Compound 1) selectively binds to each S1P receptor subtype and may be useful for the prevention or treatment of multiple sclerosis or ischemic stroke.

However, Compound 1 has very high hygroscopicity and is physically unstable after exposure to high-humidity conditions, and a new salt with greater stability than a free base of Compound 1 or a hydrochloride salt thereof has not yet been discovered. Therefore, there is a need to develop a novel salt of the compound, which is easy to formulate and overcomes the disadvantages of the above-described free base and a hydrochloride thereof and, at the same time, has excellent solid-state properties and a suppressed hygroscopicity in natural conditions, and thus has improved stability by being maintained at a constant purity even during long-term storage.

PRIOR ART DOCUMENTS

Patent Documents

Korean Patent Application Publication No. 10-2017-0087813 (Jul. 31, 2017)

DISCLOSURE

Technical Problem

An object of the present invention is to provide a novel salt of 2-amino-2-(2-(1-decyl-1H-1,2,3-triazol-4-yl)ethyl) propane-1,3-diol (Compound 1), which has a suppressed hygroscopicity in natural conditions so as to be maintained at a constant purity even during long-term storage, and is applicable to mass production while being easy to develop as a drug, and may be obtained with high purity and uniform quality, a method for preparing the same, and a pharmaceutical composition for novel uses containing the same as an active ingredient.

Technical Solution

To achieve the above object, the present invention provides a hemifumarate salt (Compound 1a, NXC736) of 2-amino-2-(2-(1-decyl-1H-1,2,3-triazol-4-yl)ethyl) propane-1,3-diol (Compound 1), which is a compound represented by Formula 1a below, and a pharmaceutical composition containing the same as an active ingredient:

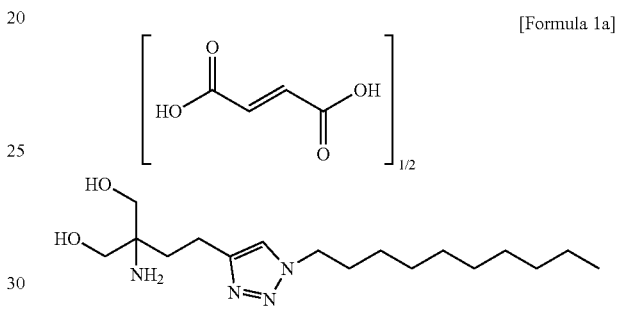

[Formula 1a]

In one embodiment of the present invention, the hemifumarate salt is in crystalline form.

In one embodiment of the present invention, Compound 1a shows an X-ray powder diffraction (XRPD) pattern having major diffraction peaks at $2\theta$ values of $6.3\pm0.2°$, $9.4\pm0.2°$, $18.5\pm0.2°$, $19.0\pm0.2°$, $19.9\pm0.2°$, $20.7\pm0.2°$, $25.5\pm0.2°$, $28.7\pm0.2°$, and $29.0\pm0.2°$.

In one embodiment of the present invention, Compound 1a exhibits a melting endothermic onset temperature of about 82° C. (82.42° C.) in differential scanning calorimetry (DSC).

In one embodiment of the present invention, Compound 1a shows a water adsorption rate of less than 2% under 90% RH conditions in DVS.

In one embodiment of the present invention, Compound 1a is maintained at a purity of 99% or higher while maintaining its crystalline form even after 2 weeks under high humidity (40° C./75±5% RH or 60° C./75±5% RH) conditions.

In one embodiment of the present invention, Compound 1a shows a purity of 98% or higher after 2 weeks under pH 6.8 phosphate buffer/40±2° C. conditions.

In one embodiment of the present invention, Compound 1a may exist as a crystalline composition.

In one embodiment of the present invention, provided is a pharmaceutical composition containing Compound 1a as an active ingredient, and the pharmaceutical composition may further contain one or more pharmaceutically acceptable carriers, diluents and/or excipients.

The present invention also provides a fumarate salt (Compound 1b) of 2-amino-2-(2-(1-decyl-1H-1,2,3-triazol-4-yl) ethyl) propane-1,3-diol (Compound 1), which is a compound represented by Formula 1b below, and a pharmaceutical composition containing the same as an active ingredient:

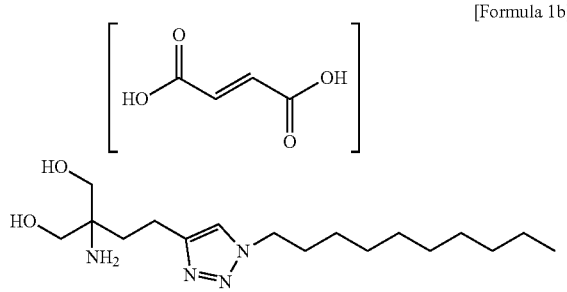

[Formula 1b]

In one embodiment of the present invention, the fumarate salt is in crystalline form.

In one embodiment of the present invention, Compound 1b shows an X-ray powder diffraction (XRPD) pattern having major diffraction peaks at 2θ values of 13.9±0.2°, 18.9±0.2°, 19.4±0.2°, 22.1±0.2°, and 22.5±0.2°.

In one embodiment of the present invention, Compound 1b exhibits a water adsorption rate of more than 3% to less than 5% under 90% RH conditions in DVS.

In one embodiment of the present invention, the pharmaceutical composition of the present invention, which contains, as an active ingredient, the novel salt of Compound 1 according to the present invention, for example, the hemifumarate or fumarate salt of Compound 1, may be useful for the prevention or treatment of multiple sclerosis, ischemic stroke, focal segmental glomerulosclerosis (FSGS), inflammatory bowel disease, interstitial fibrosis and tubular atrophy (IFTA), or alopecia areata (AA).

In one embodiment of the present invention, the inflammatory bowel disease may be ulcerative colitis (UC) or Crohn's disease (CD).

Among the above-described medicinal uses, the pharmacological effects related to multiple sclerosis and cerebral ischemia are described in Korean Patent (KR) No. 10-1830244, and the pharmacological effects related to other medicinal uses are described later.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the present invention are within the scope of the present invention.

The novel salt of Compound 1 according to the present invention exhibits excellent effects in terms of low hygroscopicity, standard stock solution stability, photostability, oxidation stability, pH-dependent stability, solubility, and the like, compared with the hydrochloride salt and other salts of Compound 1, and thus may be maintained stably without change in content or increase in impurities over a long period of time.

The novel salt of Compound 1 according to the present invention has advantages in that it is obtainable as a high-purity raw material, may be maintained at high purity for a long period of time because the increase in related substances therein is significantly low, and shows low hygroscopicity in the relative humidity range. Therefore, the novel salt is very advantageous in the processing and storage of pharmaceuticals, making it easy to formulate, and the novel salt may be maintained in the same state even after preparation of a formulation containing the same, and thus the uniformity of its content in the formulation may be maintained stably over a long period of time, indicating that the novel salt is easily applicable to mass production.

As a result of administering the novel salt of Compound 1 of the present invention orally to mice and rats, it was found that the novel salt exhibited an immunosuppressive effect. In addition, the novel salt exhibited excellent antifibrotic effects in a unilateral urinary obstruction (UUO) renal fibrosis model and an adenine-induced renal fibrosis model. Thus, the novel salt may be useful as an active ingredient of a pharmaceutical composition capable of preventing or treating multiple sclerosis, ischemic stroke, focal segmental glomerulosclerosis, inflammatory bowel disease, interstitial fibrosis and tubular atrophy, or alopecia areata (AA).

In one embodiment of the present invention, the novel salt of Compound 1 contained in the above-described pharmaceutical composition may be in crystalline form, and more specifically, may be in a crystalline form showing an X-ray powder diffraction (XRPD) pattern having major diffraction peaks at 2θ values of 6.3±0.2°, 9.4=0.2°, 18.5±0.2°, 19.0±0.2°, 19.9±0.2°, 20.7±0.2°, 25.5±0.2°, 28.7±0.2°, and 29.0±0.2°.

In one embodiment of the present invention, the pharmaceutical composition of the present invention may further contain one or more pharmaceutically acceptable carriers in addition to the novel salt of Compound 1, which is an active ingredient, for administration. As pharmaceutically acceptable carriers, saline solution, sterile water, Ringer's solution, buffered saline, dextrose solution, maltodextrin solution, glycerol, ethanol, or a mixture of one or more of these ingredients may be used, and other common additives such as antioxidants, buffers, and bacteriostatic agents may be added as needed. In addition, diluents, dispersants, surfactants, binders, and lubricants may be additionally added to prepare injectable formulations such as aqueous solutions, suspensions, emulsions, etc., pills, capsules, granules, or tablets. Accordingly, the composition of the present invention may be in the form of patches, solutions, pills, capsules, granules, tablets, suppositories, etc. These formulations may be prepared by conventional methods used for formulation in the art or by methods disclosed in Remington's Pharmaceutical Science (latest edition), Mack Publishing Company, Easton PA, and various formulations may be prepared depending on each disease or ingredient.

In one embodiment of the present invention, the pharmaceutical composition of the present invention may be administered orally or parenterally, for example, intravenously, subcutaneously, intraperitoneally, or topically, depending on the desired method, and the dosage range thereof varies depending on the patient's weight, age, gender, health status, diet, the time of administration, the mode of administration, the rate of excretion, and the severity of the disease.

In one embodiment of the present invention, provided is a method of treating multiple sclerosis, ischemic stroke, focal segmental glomerulosclerosis, inflammatory bowel disease, interstitial fibrosis and tubular atrophy, or alopecia areata, comprising administering to a subject a pharmaceutically effective amount of the novel salt of Compound 1 according to the present invention.

In one embodiment of the present invention, the novel salt of compound 1 according to the present invention, which is used in the above method, may be in crystalline form, and more specifically, may be in a crystalline form showing an X-ray powder diffraction (XRPD) pattern having major diffraction peaks at 2θ values of 6.3±0.2°, 9.4±0.2°, 18.5±0.2°, 19.0±0.2°, 19.9±0.2°, 20.7±0.2°, 25.5±0.2°, 28.7±0.2°, and 29.0±0.2°.

In one embodiment of the present invention, provided is the use of the novel salt of Compound 1 according to the present invention in the manufacture of a medicament for treatment of multiple sclerosis, ischemic stroke, focal segmental glomerulosclerosis, inflammatory bowel disease, interstitial fibrosis and tubular atrophy, or alopecia areata.

In one embodiment of the present invention, the novel salt of compound 1 according to the present invention, which is used in the above-described use, may be in crystalline form, and more specifically, may be in a crystalline form showing an X-ray powder diffraction (XRPD) pattern having major diffraction peaks at 2θ values of $6.3\pm0.2°$, $9.4\pm0.2°$, $18.5\pm0.2°$, $19.0\pm0.2°$, $19.9\pm0.2°$, $20.7\pm0.2°$, $25.5\pm0.2°$, $28.7\pm0.2°$, and $29.0\pm0.2°$.

Advantageous Effects

The novel salt of 2-amino-2-(2-(1-decyl-1H-1,2,3-triazol-4-yl)ethyl)propane-1,3-diol (Compound 1) according to the present invention exhibits excellent effects in terms of hygroscopicity, standard stock solution stability, photostability, oxidation stability, pH-dependent stability, solubility, and the like, compared to the hydrochloride salt and other salts of Compound 1, and the pharmaceutical composition of the present invention, which contains the novel salt as an active ingredient, may be useful for the prevention or treatment of multiple sclerosis, ischemic stroke, focal segmental glomerulosclerosis, inflammatory bowel disease, interstitial fibrosis and tubular atrophy, or alopecia areata.

BRIEF DESCRIPTION OF DRAWINGS

FIG. 1 shows DSC data of Compound 1a.
FIG. 2 shows DVS data of Compound 1a.
FIG. 3 shows XRPD data of Compound 1a.
FIG. 6 depicts graphs showing the effect of Compound 1a (5 and 10 mg/kg/day) on suppression of inflammatory bowel disease in a DSS-induced colitis mouse model.
FIG. 7 is a table showing the results of evaluating the effect of Compound 1a (1, 3, 10, and 30 μM) on HEK293 cells overexpressing the hERG gene.
FIG. 11 depicts photographs showing the results of observing changes in the appearances of the free base of Compound 1, Compound 1a, and the hydrochloride salt of Compound 1 initially and 2 weeks after storing each of them under 60° C./75% RH conditions.

DETAILED DESCRIPTION

General Definition and Terminology

Figure 1:
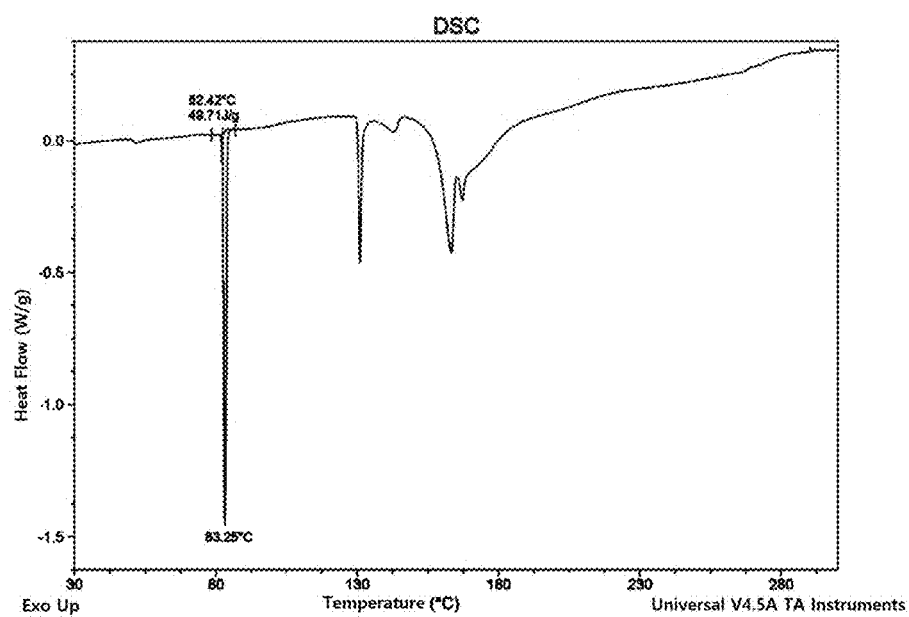
Figure 2:
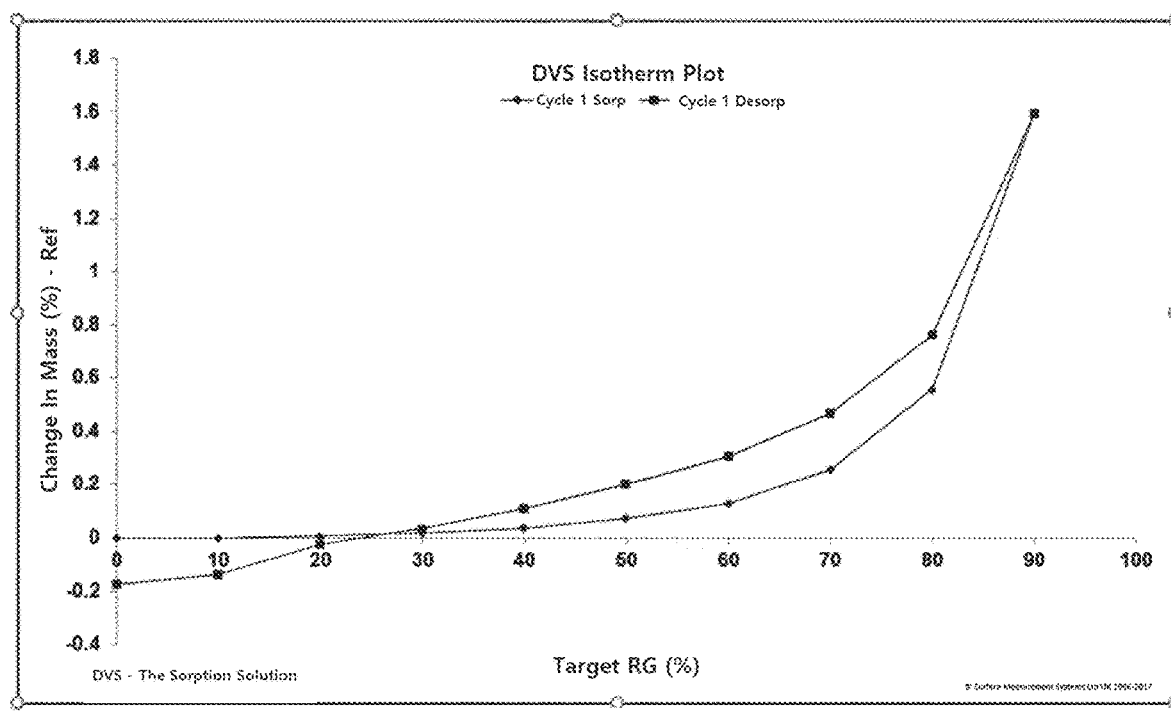
Figure 3:
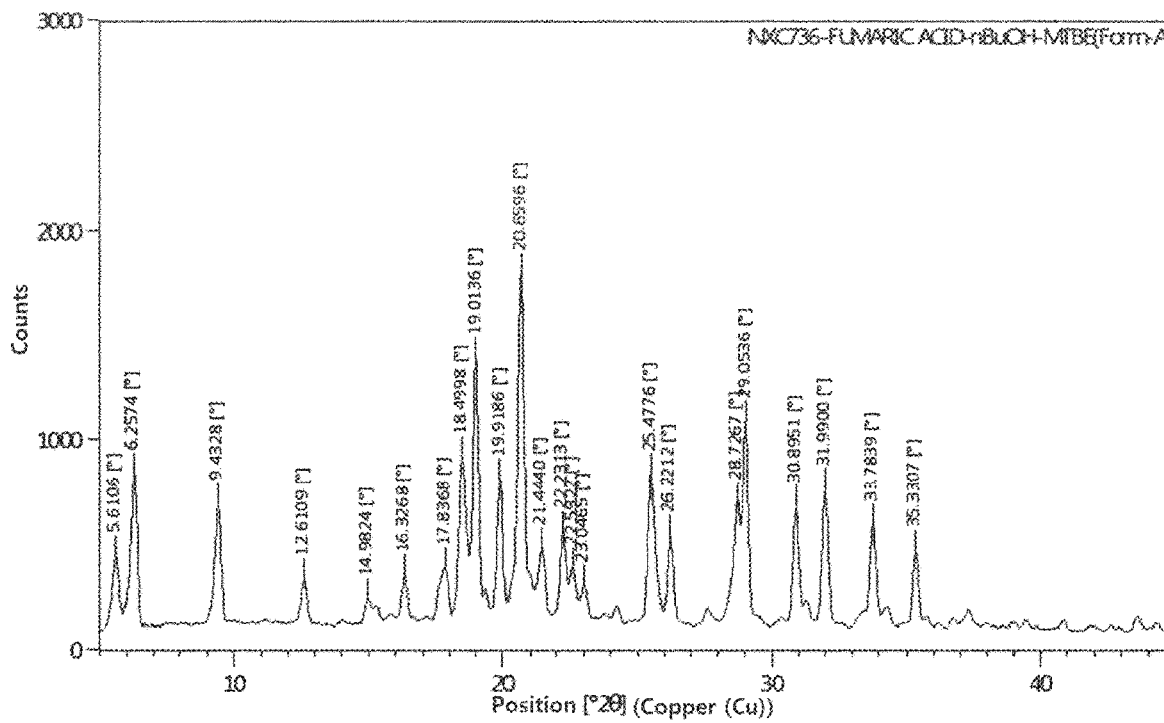

Unless specifically defined otherwise, proportion (including percentage) or part is calculated based on weight herein.

As used herein, the expression "comprise" or its synonyms "contain", "include", "have" or the like is open-ended, which does not exclude other unlisted elements, steps or ingredients.

The use of the term "about" includes and describes the value or parameter per se. For instance, "about x" includes and describes "x" per se. In some embodiments, the term "about" when used in association with a measurement, or used to define a value, a unit, a constant, or a range of values, refers to a variation of ±1%±10%, unless indicated otherwise. For example, "about 82° C." in some embodiments includes 82° C. to 83° C.

The term "pharmaceutical composition" refers to an active ingredient, which is optionally combined with one or more pharmaceutically acceptable components (for example, but not limited to, carrier and/or excipient). The active ingredient is exemplified as the compound of Formula I or the hemifumarate thereof, one or more crystal forms according to the present invention, or one or more crystalline composition according to the present invention.

The term "administration" or "administrating" or the like refers to a method that enables a compound or composition to be delivered to a desired site of biological action. Such methods include, but not limited to, oral, parenteral (including intravenous, subcutaneous, intraperitoneal, intramuscular, intravascular injection or infusion), local, rectal administration, or the like.

As for pharmaceutical or pharmacological active agent, the term "effective amount" refers to the amount of the medicament or agent which is not toxic but sufficient to achieve the desired effect. With respect to the oral formulation herein, the "effective amount" for an active substance in the composition refers to the amount required to achieve the desired effect in combination with another active substance in the composition. The effective amount may be determined individually and may depend on the age and general condition of the receptor as well as specific active substance. The effective amount in a specific case may be determined by a person skilled in the art through conventional test.

The term "active ingredient", "therapeutic agent", "active substance" or "active agent" refers to a chemical entity useful for treating or preventing target disorder, disease or condition effectively. The term herein may refer to, for example, the compound of Formula I or the hemifumarate thereof, one or more crystal forms according to the present invention or one or more crystalline compositions according to the present invention.

The term "low hygroscopicity" as used in the present invention refers to the property of a substance that neither absorbs nor adsorbs water from the air, which is in contrast to hygroscopicity referring to the ability of a substance to attract and hold water molecules from the surrounding environment.

The term "stability" as used in the present invention is a term that indicates the degree to which the salt of the compound represented by Formula 1 according to the present invention or a composition containing the same is chemically or physically stable under specific conditions for a specific time. The purpose of stability testing is to provide evidence of how the quality of the salt of the present invention changes with time under the influence of various environmental factors such as temperature, humidity, and light, and to establish and to establish the period of use (or expiration date) and recommended storage conditions of the finished drug product manufactured using the salt.

The standards for stability testing of pharmaceuticals, etc., provided by the Korean Ministry of Food and Drug Safety, prescribe "stress testing" for identifying the decomposition process and decomposition products of pharmaceuticals, etc. under stress conditions, and describe that, as conditions for the stress testing, light, temperature and humidity conditions should be set in consideration of the characteristics of the sample, and if the sample is a raw material, test conditions in an aqueous solution state should be included, and the effects of oxidation and photodecomposition on the active pharmaceutical ingredient and the pH-dependent susceptibility to hydrolysis should be evaluated.

Accordingly, among the stability test standards of the present invention, "standard stock solution stability" is assessed by dissolving the salt of the present invention in a standard stock solution, storing the resulting solution for a specific period of time under specific temperature and humidity conditions, and then checking the purity of the salt to determine whether related substances (impurities) occurred. In addition, the "photostability", "oxidation stability", and "pH-dependent stability" of the salt of the present invention were evaluated under the specific conditions specified in the Examples below.

In X-ray powder diffraction (XRPD or XRD) spectra, the diffraction pattern obtained from a crystalline compound is generally characteristic for a particular crystal form in which the relative intensities of the bands (especially at low angles) may vary with the dominant orientation effect due to the difference of crystallization conditions, particle diameters, and other measuring conditions. Therefore, the relative intensities of diffraction peaks are not characteristic for the given crystal form. It is more important to note the relative positions of peaks rather than their relative intensities when determining whether the crystal form is the same as that known in the art. In addition, there may be slight errors in the positions of the peaks for any given crystal form, which is also well known in the art of crystallography. For example, the position of the peak may shift due to the change in temperature, sample movement or instrument calibration during analysis of the sample; and the measuring error of $2\theta$ value may sometimes be about $\pm 0.2°$, typically about $\pm 0.1°$. Therefore, this error should be taken into account when determining the crystal structure. If the crystal forms according to the invention are described as substantially as shown in the figure, the term "substantially" is also intended to encompass such differences in the diffraction peak.

In the XRPD pattern, the peak position is usually represented by angle $2\theta$ or crystal surface distance d and a simple conversion between d and $\theta$ is $d=\lambda/2 \sin \theta$, where d represents the crystal surface distance, $\lambda$ represents the wavelength of the incident X-ray, and $\theta$ is diffraction angle. As for the same crystal form of the same compound, the peak positions of the XRPD pattern are similar as a whole, and the relative intensity error may be large. It should also be noted that, in identification of a mixture, some diffraction lines may be lost due to the factors like decrease in content, etc., and thus it is not necessary to rely on the entire bands observed in the high purity sample, and even one band may be characteristic for a given crystal.

Differential scanning calorimetry (DSC) is used to measure the transition temperature when a crystal absorbs or releases heat due to changes in its crystal structure or crystal melting. The thermal transition temperature and the melting point error are typically within about 5° C., usually about 3° C. for the same crystal form of the same compound in a continuous analysis. When a compound is described as having a given DSC peak or melting point, it means the DSC peak or melting point ±5° C. Provided is an auxiliary method by DSC to identify different crystal forms. Different crystal forms may be identified according to their different transition temperature characteristics. The DSC peak or melting point of the mixture may vary over a wide range. In addition, the melting temperature is associated with the rate of temperature rise due to the decomposition during the melting of the substance.

Dynamic vapor sorption (DVS) is a method that has been used for a long time to investigate the interactions between active pharmaceutical ingredients (APIs), and pharmaceutical preparations and water. Here, to analyze the water absorption rate of a sample at a specific temperature, measurements are made by exposing the sample to the desired relative humidity using a DVS water sorption analyzer (hygroscopicity analyzer) until the change in weight of the sample stabilizes.

The method for preparing the salt of the present invention and the process of selecting the salt thereby are as follows. First, the free base of Compound 1 was found to have some basicity (pKa=8.12) in natural conditions, and thus various methods were used to select an acid that could be an appropriate match among acidic counterions. Specifically, acids that were appropriate for matching the pKa of the free base of Compound 1 described above were calculated by computer, and these acids were mainly identified as acids having a pKa of about 2 to 5.

Accordingly, a total of 22 types of crystalline solids were obtained by conducting various experiments using acids in the above range together with various types of solvents, their respective crystallinity was examined, and DSC and DVS analyses were performed. As a result, it was found that the hemifumarate or fumarate was the best salt in terms of crystallinity, melting point, hygroscopicity, etc.

Sphingosine-1-phosphate (S1P) receptors 1-5 constitute a family of G protein-coupled receptors with seven transmembrane domains. These receptors, referred to as S1P1 to S1P5, are activated via binding by sphingosine-1-phosphate, which is produced by the sphingosine kinase-catalyzed phosphorylation of sphingosine. S1P1, S1P4, and S1P5 receptors activate Gi but not Gq, whereas SIP2 and S1P3 receptors activate both Gi and Gq. The S IP3 receptor, but not the S1P1, responds to an agonist with an increase in intracellular calcium.

2-Amino-2-(2-(1-decyl-1H-1,2,3-triazol-4-yl)ethyl)propane-1,3-diol compound (hereinafter referred to as Compound 1) binds selectively to each S1P receptor subtype and acts as a functional antagonist to reduce lymphocytes in peripheral blood.

Compound 1 is useful for the treatment of multiple sclerosis and ischemic stroke. See Korea Patent Application Publication No. 10-2017-0087813, which is incorporated herein by reference.

Meanwhile, inflammatory bowel disease is a chronic disease in which abnormal inflammation occurs repeatedly within the intestine. It is caused by an immune response to intestinal flora, and representative examples thereof include "ulcerative colitis" and "Crohn's disease". It mainly occurs in Westerners, and as Asian eating habits gradually become westernized, the number of domestic patients is also increasing. Ulcerative colitis was a disease with a high incidence in Europe and North America, where people mainly eat meat, but recently, the incidence thereof has also been increasing in East Asia, including South Korea, due to westernized eating habits. Crohn's disease is a chronic inflammatory bowel disease that can occur anywhere throughout the digestive tract from the mouth to the anus, and there is still no drug therapy that can completely cure ulcerative colitis.

In addition, in 2015, there were about 120,700 organ transplants worldwide, which increased by 5.8% compared to those in the previous year, and approximately 60% thereof were kidney transplants. Interstitial fibrosis and tubular atrophy (IFTA) occurs in approximately 25% of patients one year after renal transplantation. As the interstitial space expands and replaces normal tissue due to histopathological changes in the transplanted kidney, tubular atrophy and interstitial fibrosis occur, causing a decrease in glomerular filtration rate and an increase in proteinuria. It occurs in 66% of cases at 5 years after transplantation and up to 90% at 10 years after transplantation. In the early stages, these symptoms are mainly caused by immunological factors, but in the later stages, they are mainly attributed to the toxicity of calcineurin inhibitors, which are immunosuppressants.

Although the mechanism by which calcineurin inhibitors, which are mainly used as immunosuppression maintenance therapy after transplantation, cause IFTA is not clear, these calcineurin inhibitors are known to cause fibrosis by causing vasoconstriction, oxidative stress, and TGF-β.

Currently, calcineurin inhibitors, antimetabolites, steroid combination therapy, etc. in addition to calcineurin inhibitors are being used for chronic transplant rejection. However, there has not yet been a clearly established treatment method for IFTA. Thus, if a drug that exhibits both immunosuppressive and antifibrotic effects is developed, the drug is expected to improve the quality of life of patients after transplantation.

Focal segmental glomerular sclerosis (FSGS) is a disease that causes filtration disorder and proteinuria by structural damage to podocytes (e.g., sclerosis), which are the renal filtration system, and is the most common cause of end-stage renal failure. The number of patients worldwide is more than 300,000, and the number of patients in the United States is about 80,000, accounting for one-third of adult nephrotic syndrome cases. Currently, steroids, immunosuppressants, and angiotensin receptor blockers are used, but they cause serious complications such as renal failure and anemia. Thus, it is necessary to develop drugs that overcome the side effects of existing FSGS treatments and have improved efficacy.

Alopecia areata is a disease in which the hair falls out in a circular shape. Alopecia areata may show circular hair loss in one or two areas, or in severe cases, may occur in several areas at the same time. Alopecia areata shows a phenomenon in which hair loss areas are fused and eyebrows or beard hairs also lost in addition to the hair on the scalp. Loss of hair on the entire scalp is called alopecia totalis, and loss of hair not only on the scalp but also on the entire body is called alopecia universails. Hair loss that occurs in a band shape along the outer circumference of the temporal and occipital regions is called ophiasis. Alopecia areata is an autoimmune disease in which the immune system changes, causing immune cells to attack hair follicles and cause inflammation. Alopecia areata is believed to be caused by stress and genetic factors. In less than 10% of patients with alopecia areata, alopecia areata may be accompanied by other autoimmune diseases such as atopic dermatitis, thyroid disease, and pernicious anemia. Although alopecia areata occurs in men and women and all age groups, it is the most common disease among children and young adults and has a prevalence of about 1-2% of the total population.

Representative treatments for alopecia areata are steroids. Steroid injections, steroid medications, immunosuppressants, etc. have been approved and used as therapeutic agents, but they are used for treatment over a long period of time, they are initially effective to some extent, but they worsen symptoms or cause major side effects such as scalp inflammation, scalp depression, hypertension, weight gain, heartburn, and gastritis, and symptoms tend to relapse. Olumiant (ingredient name: Baricitinib), an oral JAK inhibitor currently known globally as a therapeutic agent for rheumatoid arthritis, was approved as the first systemic treatment for alopecia areata by the U.S. Food and Drug Administration in June 2022. Following this, Pfizer, the world's No. 1 pharmaceutical company, also announced efficacy data similar to Olumiant after completing the phase 3 trial of PF-06651600 (ingredient name: Ritlecitinib), a type of JAK inhibitor. Pfizer applied for marketing approval of Ritlecitinib to the FDA based on the results that major adverse cardiac events (MACE) and infectious side effects, which are of concern during long-term administration of JAK inhibitors, especially in terms of safety, were not observed. Accordingly, there is a continuous need for the development of drugs that can be used to treat alopecia areata, have excellent efficacy, and are safe in terms of side effects or toxicity.

Accordingly, the present inventors have made extensive efforts to develop an independent compound that selectively acts on the S1P subtype receptors among sphingolipid compounds. As a result, the present inventors have found that the compound according to the present invention binds specifically to the S1PR1 and S1PR4 receptors and acts as a functional antagonist for the receptors, and thus has effects of preventing and treating focal segmental glomerulosclerosis, interstitial fibrosis and tubular atrophy, inflammatory bowel disease, and alopecia areata without causing cardiovascular disease side effects due to non-selectivity for the S1PR subtype, thereby completing the present invention.

Hereinafter, the present invention will be described in more detail with reference to examples. However, the following examples are intended to illustrate the present invention in more detail, and the scope of the present invention is not limited by the following examples. The following examples may be appropriately modified and changed by those skilled in the art within the scope of the present invention.

Example 1: Preparation of Hemifumarate Salt of 2-amino-2-(2-(1-decyl-1H-1,2,3-triazol-4-yl)ethyl) propane-1,3-diol (Compound 1)

98 mg (0.55 equivalent) of fumaric acid and 500 mg of the free base of Compound 1 were added to 25 mL of methyl isobutyl ketone (MIBK) (23.9 mg/mL) and mixed with stirring at room temperature for 5 minutes. The resulting suspension was subjected to the following cooling crystallization process. First, the suspension was heated at 40° C. for 10 hours and then stirred at 5° C. for 12 hours. Upon completion of the reaction a thick white suspension was formed. The solid material in the suspension was centrifuged, and the precipitate was separated and dried under vacuum (−700 mmHg conditions) at room temperature for 16 hours to obtain 525.5 mg (89.2%) of the final product.

The prepared hemifumarate salt showed an X-ray powder diffraction (XRPD) pattern having manor diffraction peals at 2θ values of 6.3±0.2°, 9.4±0.2°, 18.5±0.2°, 19.0±0.2°, 19.9±0.2°, 20.7±0.2°, 25.5±0.2°, 28.7±0.2°, and 29.0±0.2°.

$^1$H-NMR (DMSO-d6): δ 0.8 (3H, t), 1.2 (15H, m), 1.75 (4H, m), 2.65 (2H, m), 3.4 (4H, t), 4.25 (2H, t), 6.4 (1H, m), 7.8 (1H, s)

In the $^1$H-NMR data, the proton number (based on integrated values) of >CH protons of fumarate appearing at δ 6.4 ppm was calculated as half of the number of protons of the corresponding free base, indicating that the ratio of the salt in the final product was 1:0.5.

Example 2: Preparation of Fumarate Salt of 2-amino-2-(2-(1-decyl-1H-1,2,3-triazol-4-yl)ethyl)propane-1,3-diol (NXC736)

196 mg (1.1 equivalent) of fumaric acid and 500 mg of the free base of NXC736 were added to 25 mL of acetone and mixed with stirring at room temperature for 5 minutes. The resulting suspension was subjected to the same cooling crystallization process as in Example 1 and dried under vacuum (−700 mmHg conditions) to obtain 562 mg of the final product.

The final product fumurate showed an X-ray powder diffraction (XRPD) pattern having major diffraction peaks at 2θ of 13.9±0.2°, 18.9±0.2°, 19.4±0.2°, 22.1±0.2°, and 22.5±0.2°.

Comparative Examples 1 to 6: Preparation of Other Salts of Compound 1

Salts of Compound 1 were prepared by mixing various acids and the free base of Compound 1, and the acids and solvents used are shown in Table 1 below.

Experimental Example 1: Hygroscopicity Test

The characteristics of the salts prepared in Comparative Examples 1 to 6 and the novel salts of the present invention were analyzed by the DVS method, and the results are shown in Table 1 below.

TABLE 1

Comparison of hygroscopicity between the Examples of the present invention and other salts

| Sample name | | Solvent used for preparation | XRPD remark | DVS remark (adsorption at 90% RH) |
|---|---|---|---|---|
| Example 1 | Compound 1/ Fumaric acid | MIBK | Crystalline | 1.595% |
| Example 2 | Compound 1/ Fumaric acid | Acetone | Crystalline | 4.563% |
| Comparative Example 1 | Compound 1/HCl | MIBK | Crystalline | 49.5% |
| Comparative Example 2 | Compound 1/ Succinicacid | Acetonitrile | Crystalline | 19.42% |
| Comparative Example 3 | Compound 1/ Acetic acid | Acetonitrile | Crystalline | 34.33% |
| Comparative Example 4 | Compound 1/ Acetic acid | MIBK | Crystalline | 33.67% |
| Comparative Example 5 | Compound 1/ Adipic acid | MIBK | Crystalline | 22.46% |
| Comparative Example 6 | Compound 1/ Citric acid | Acetone | Crystalline | 22.80% |

According to the results of DVS analysis of the hydrochloride salt of Compound 1 (Comparative Example 1), the compound showed a water adsorption rate of 49.5% at 90% RH and exhibited deliquescence in natural conditions. In addition, the salts of Comparative Examples 2 to 6 were also shown to have relatively very high hygroscopicity.

On the other hand, it was found that, compared to Comparative Examples 1 to 6, Example 1 showed a water adsorption rate of less than 2% at 90% RH as a result of DVS evaluation, indicating that it had very low hygroscopicity.

In addition, as a result of DVS evaluation which was repeated several times, it was found that Example 2 showed a water vapor adsorption rate of more than 3% to than 5% at 90% RH, indicating that it had low hygroscopicity.

Example 2: Solubility Study of Compound 1a

The solubility of Compound 1a prepared in Example 1 was evaluated in several different media, including pH 1.2 hydrochloric acid buffer, pH 3.0 citrate buffer, pH 4.7 acetate buffer, pH 6.8 phosphate buffer, simulated gastric fluid, fasted-state simulated intestinal fluid, fed-state simulated intestinal fluid, and water. About 2.17 mg of sample (based on the free base of Compound 1) for each medium was taken into a 2-mL transparent glass vial and 0.5 mL of medium was added (constituents of the salt were considered Compound 1: counterion=1:0.5; target concentration: 2 mg/mL). The mixture was stirred using a magnetic stirrer at 250 RPM for 24 hours at 25° C. Next, the pH and appearance of the mixture were recorded and the mixture was filtered through a MultiScreen® HTS-HV 96-well plate (manufactured by Merck; 0.45-μm hydrophilic, low-protein-binding Durapore® membrane). Solubility was determined using HPLC, and a calibration curve was created by injecting a known concentration of Compound 1a. The filtered sample was injected (diluted appropriately as necessary) and the concentration of Compound 1a (mg/mL) in the filtrate was calculated from the calibration curve (taking salt coefficient into account). The analysis results are as follows.

TABLE 2

Solubility evaluation results for Compound 1a in aqueous media

| Media | Visual observation | Solubility (mg/mL) | Final pH |
|---|---|---|---|
| pH 1.2 HCl buffer | Clear solution | >2 | 1.75 |
| pH 3.0 Citrate buffer | Clear solution | >2 | 3.42 |
| pH 4.7 Acetate buffer | Clear solution | >2 | 5.11 |
| pH 6.8 Phosphate buffer | White suspension | 0.306 | 6.94 |
| SGF (pH 2.0) | Clear solution | >2 | 3.02 |

TABLE 2-continued

Solubility evaluation results for Compound 1a in aqueous media

| Media | Visual observation | Solubility (mg/mL) | Final pH |
|---|---|---|---|
| FaSSIF (pH 6.5) | Clear solution | >2 | 6.60 |
| FeSSIF (pH 5.8) | Clear solution | >2 | 5.97 |
| Water | Clear solution | >2 | 6.04 |
| 0.5% Methylcellulose | Clear solution | >2 | 6.04 |

It was shown that the solubility of Compound 1a was more than 2 mg/mL in all of the above-mentioned aqueous media, except for phosphate buffer (pH 6.8), and substantially the entire sample was completely dissolved, but the hydrochloride salt of Compound 1 under the same conditions was in undissolved suspension form in some samples.

Experimental Example 3: Stability Study

The standard stock solution stability, pH stability, salinity stability, photostability, and oxidation stability of Compound 1a were examined under various conditions as follows.

Example 3-1: Study of Standard Stock Solution Stability—40° C./75±5% RH Conditions The stability of the crystalline compound was examined at 40° C./75±5% RH. Physical stability was examined through comparative XRPD analysis before and after the test, and chemical stability was examined by HPLC method. The experimental conditions used in the stability test for Compound 1a and the test results are as follows.

Stability Conditions and Test Methods:
40° C./75±5% RH: Conditions in which the vial was open and upright.

A required amount (~1 mg) of solid material was dissolved in 1 mL of a diluent (1:1 methanol/water), and the prepared solution was analyzed by HPLC.

TABLE 3

Results of standard stock solution stability test for hydrochloride salt of Compound 1

| | | Hydrochloride salt of Compound 1 | |
|---|---|---|---|
| Stability Conditions | | Purity % | XRPD |
| 40° C./75% RH | Initial | 99.34 | Crystalline |
| | 1-week | 99.00 | Turned into liquid |
| | 2-week | 99.22 | NA |

TABLE 4

Results of standard stock solution stability test for Compound 1

| | | Compound 1a | |
|---|---|---|---|
| Stability Conditions | | Purity % | XRPD |
| 40° C./75% RH | Initial | 99.29 | Crystalline |
| | 1-week | 99.18 | Almost similar (some changes observed below 5°2θ) |
| | 2-week | 99.42 | Almost similar (some changes observed below 5°2θ) |

As shown in Table 3 above, the hydrochloride salt of Compound 1 turned into a liquid phase, considered physically unstable, after a week under high humidity (40° C./75±5% RH) conditions, and some samples showed deliquescence. However, referring to Table 4 above, it was found that, in the case of Compound 1a, the crystalline form was maintained even after 2 weeks under high humidity (40° C./75±5% RH) conditions, and the purity was maintained at more than 99%, indicating that the stability of the standard stock solution was excellent.

Experimental Example 3-2: Study of Standard Stock Solution Stability-60° C./75±5% RH Conditions The stability of the crystalline compound was under 60° C./75±5% RH conditions, and the purity thereof was examined by HPLC method. The experimental conditions used in the stability test for Compound 1a and the test results are as follows.

Stability Conditions and Test Methods:
60° C./75±5% RH: Conditions in which the vial was open and upright.

A required amount (~1 mg) of solid material was dissolved in 1 mL of a diluent (1:1 methanol/water), and the prepared solution was analyzed by HPLC.

TABLE 5

Results of standard stock solution stability test for Compound 1a

| | | Purity % | |
|---|---|---|---|
| Stability Conditions | | Free base | Compound 1a |
| 60° C./75% RH | Initial | 98.19 | 99.11 |
| | 1-week | 97.73 | 98.72 |
| | 2-week | 96.96 | 98.55 |

Referring to Table 5 above, it can be seen that, in the case of Compound 1a, the generation of related substances and change in content after 1 and 2 weeks under high-humidity (60° C./75±5% RH) conditions were very low compared to those in the free base of Compound 1, and the purity was maintained at more than 98%, indicating that the stability of the standard stock solution was relatively excellent.

Figure 12:
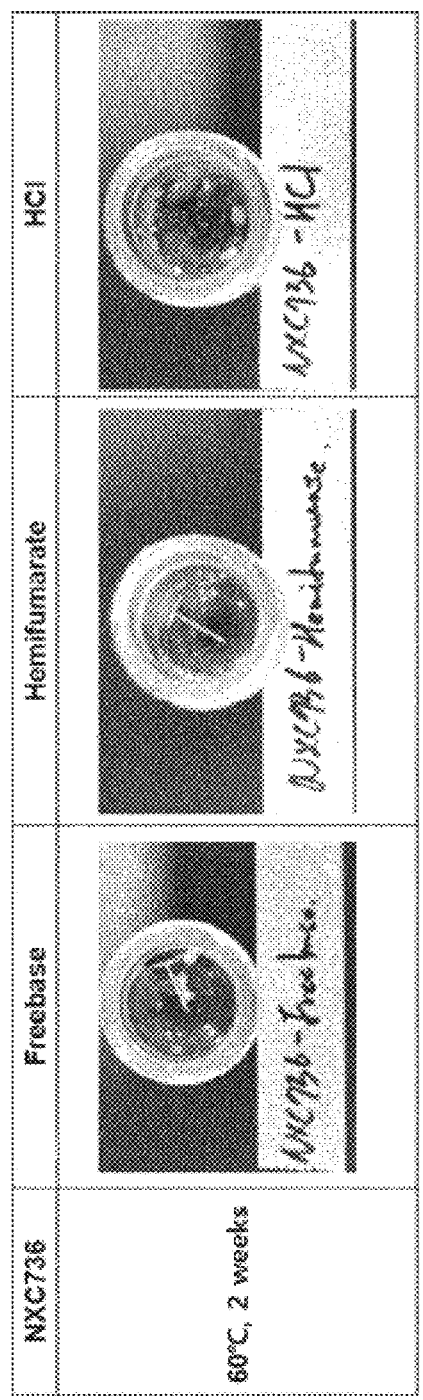
FIG. 12 depicts photograph showing the results of checking the degree of corrosion of a sample after storing each of the free base of Compound 1, Compound 1a, and a hydrochloride salt of Compound 1 together with the sample under 60° C. conditions for 2 weeks.
Figure 13:
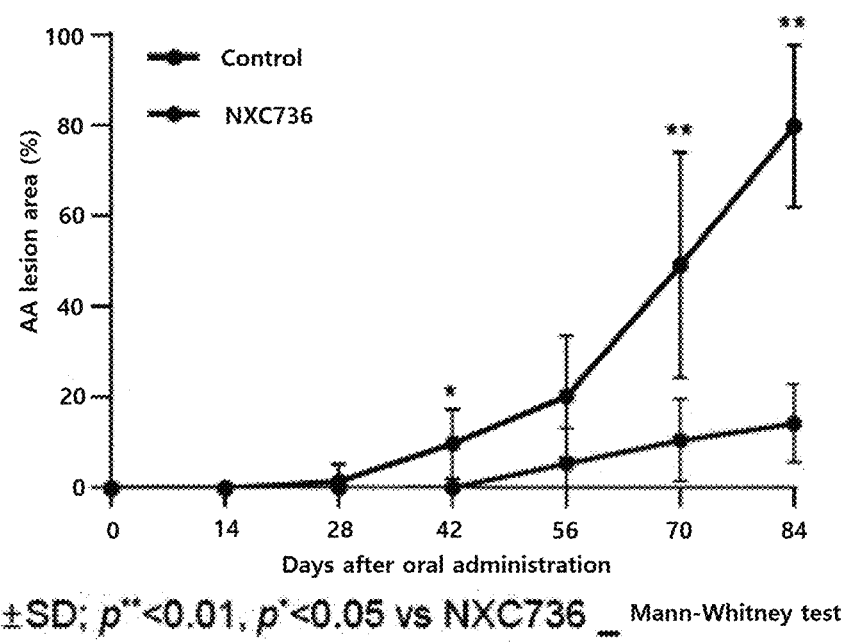
FIG. 13 shows the results of measuring the alopecia areata (AA) lesion area after administrating 30 mg/kg of Compound 1a orally to 10-16-week-old C3H/HeJ mice with induced alopecia areata for 12 weeks.
Figure 14:
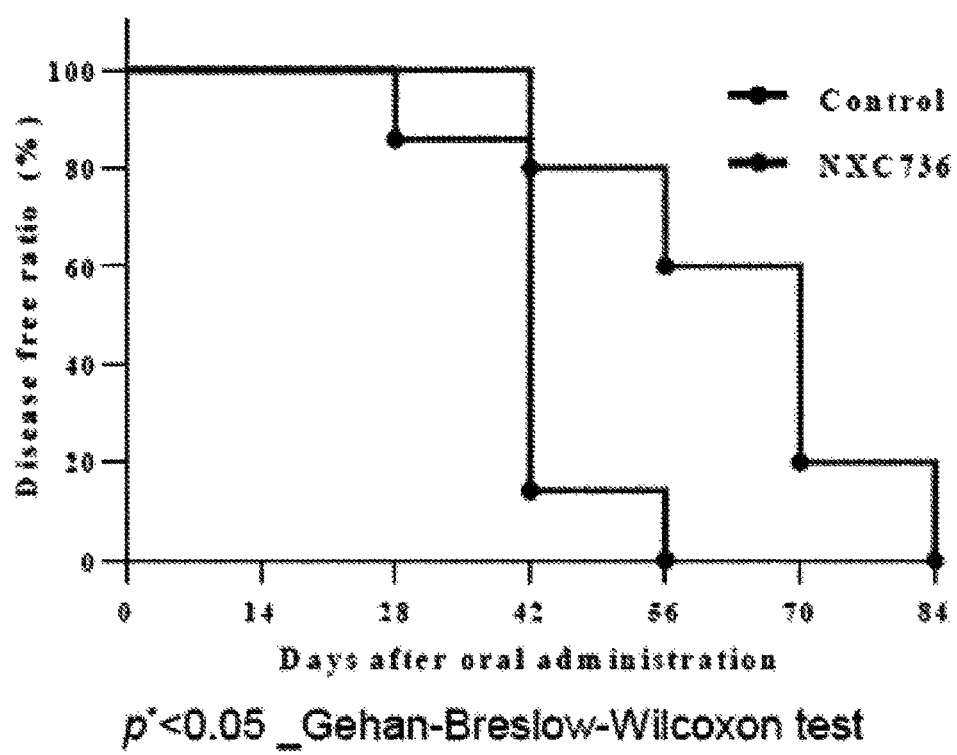
FIG. 14 shows the results of measuring the disease-free ratio after administrating 30 mg/kg of Compound 1a orally to 10-16-week-old C3H/HeJ mice with induced alopecia areata for 12 weeks.
Figure 15:
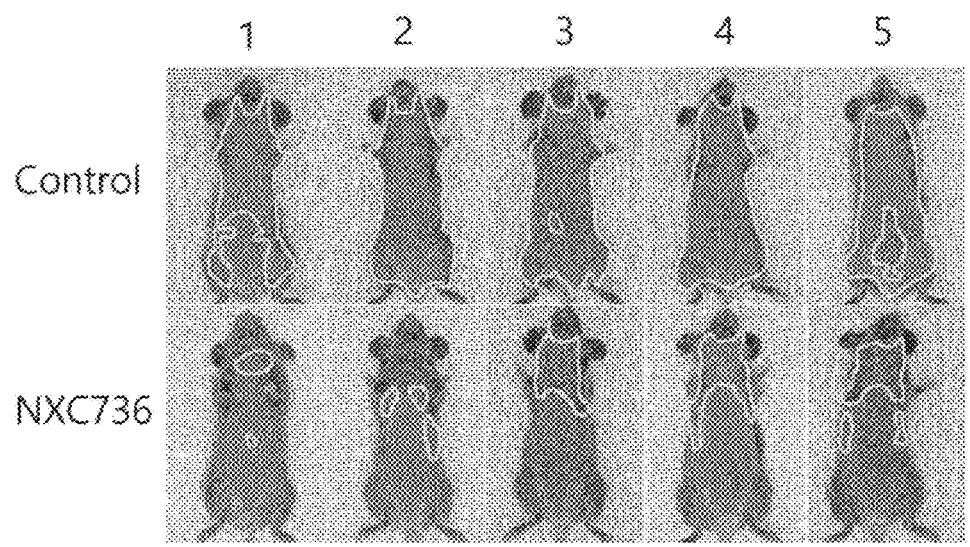
FIG. 15 shows photographs comparing the induction of alopecia areata after administering compound 1a to 10-16-week-old C3H/HeJ mice with induced alopecia areata.
Figure 16:
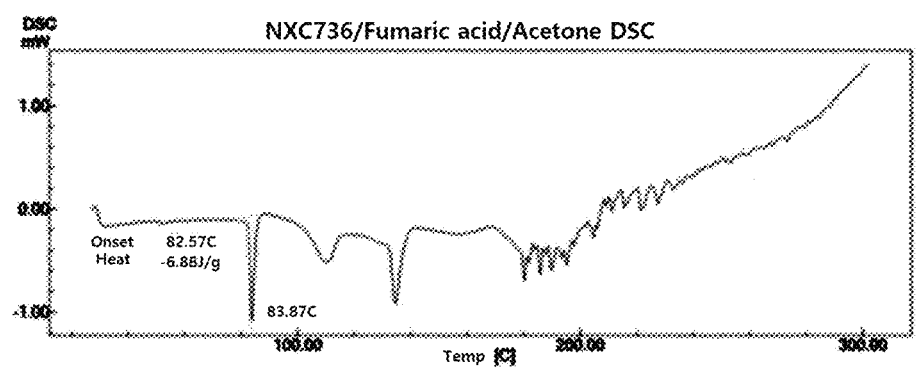
FIG. 16 shows DSC data of Compound 1b.
Figure 17:
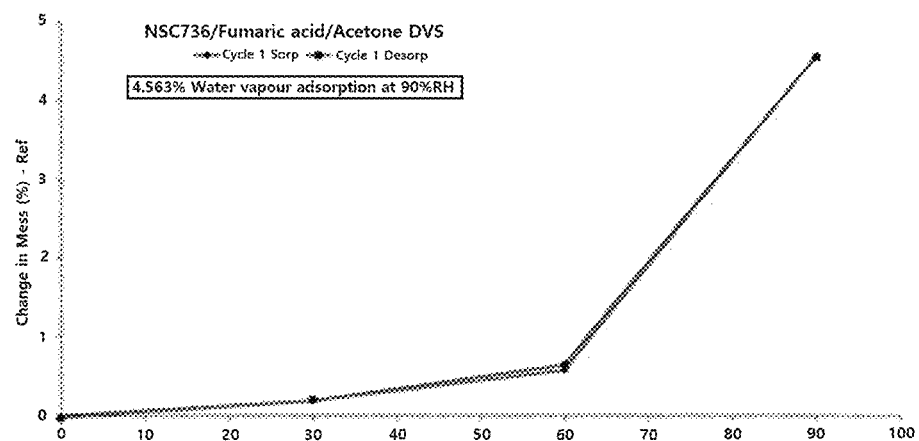
FIG. 17 shows DVS data of Compound 1b.

FIG. 11 depicts photographs showing the results of observing changes in the appearances of the free base of Compound 1, Compound 1a, and the hydrochloride salt of Compound 1 initially and 2 weeks after storing each of them under 60° C./75±5% RH conditions, and it can be seen that the hydrochloride salt turned into a liquid phase by absorbing water. In addition, as shown in FIG. 12, as a result of checking the degree of corrosion of the sample after storing the free base of Compound 1, Compound 1a, and the hydrochloride salt of Compound 1 together with the sample for 2 weeks at 60° C., it was found that corrosion occurred in the case of the hydrochloride salt, suggesting that water absorption by the hydrochloride salt occurred.

Experimental Example 3-3: pH Stability and Salinity Stability pH and salinity stability tests for the hemifumirate salt of Compound 1 were performed at an initial target concentration of 2 mg/mL. The pH and salinity stability conditions used to evaluate the hemifumirate salt of Compound 1 and the evaluation results are as follows.

Stability Conditions and Test Method:
- 40±2° C.: Conditions in which the vial was capped and upright
- Storage container for stability: 2-mL screw neck clear glass vial (manufactured by La-Pha-Pack)
- Target concentration: ~ 2 mg/mL (adding the sample to 1 mL of medium, followed by vortexing for 30 seconds)
- 500 μL of the test mixture was dissolved in 500 μL of a diluent (1:1 methanol/water), and the prepared solution was analyzed by HPLC without filtration.

TABLE 6

Evaluation of pH stability and salinity stability of hydrochloride salt of Compound 1

| Stability Conditions | | Hydrochloride salt of Compound 1 Purity % |
|---|---|---|
| pH 6.8 phosphate buffer/40° C. | Initial | 98.93 |
| | 1-week | 98.04 |
| | 2-week | 97.87 |
| Saline (0.9% NaCl)/40° C. | Initial | 99.43 |
| | 1-week | 98.00 |
| | 2-week | Ongoing |

TABLE 7

Evaluation of pH stability and salinity stability of hydrochloride salt of Compound 1a

| Stability Conditions | | Compound 1a Purity % |
|---|---|---|
| pH 1.2 HCl buffer/40° C. | Initial | 98.92 |
| | 1-week | 98.26 |
| | 2-week | 98.76 |
| pH 4.7 acetate buffer/40° C. | Initial | 99.23 |
| | 1-week | 99.46 |
| | 2-week | 99.69 |
| pH 6.8 phosphate buffer/40° C. | Initial | 99.20 |
| | 1-week | 98.36 |
| | 2-week | 98.23 |
| SGF/40° C. | Initial | 99.13 |
| | 1-week | 99.25 |
| | 2-week | 99.29 |
| Saline (0.9% NaCl)/40° C. | Initial | 99.20 |
| | 1-week | 99.05 |
| | 2-week | Ongoing |

As can be seen in Table 7 above, Compound 1a showed a purity of more than 98% after 2 weeks under pH 6.8 phosphate buffer/40±2° C. conditions, and the purity thereof tended to remain the same in most cases despite various changes in pH and addition of saline, indicating that Compound 1a generally showed excellent pH stability and salinity stability.

However, referring to Table 6 showing the data of the hydrochloride salt of Compound 1 under the same conditions, it was found that the hydrochloride salt of Compound 1 showed a purity of less than 98% after 2 weeks under pH 6.8 phosphate buffer/40±2° C., and showed a purity of 98% or less even 1 week after addition of saline.

Accordingly, it could be found that Compound 1a had relatively excellent pH stability and salinity stability compared to the hydrochloride salt of Compound 1.

Experimental Example 3-3: Photostability and Oxidation Stability

For a photostability test, 10 mg of Compound 1a was exposed to 1.2 million lux hours of ultraviolet and visible light at room temperature. For an oxidation stability test, 0.2 mL of 30% $H_2O_2$ and 1 mg of Compound 1a were placed in a 2-mL vial and stored at 25° C. for up to 24 hours. The photostability and oxidation stability conditions used to evaluate the fumarate salt of Compound 1 and the evaluation results are as follows.

TABLE 8

Photostability and oxidation stability test results for hydrochloride salt of Compound 1

| | Stability Conditions | Hydrochloride salt of Compound 1 Purity % | XRPD |
|---|---|---|---|
| Photostability | Photostability 1.2 million lux hours exposed | 98.75 | Same as initial |
| | Photostability 1.2 million lux hours unexposed | 99.35 | Same as initial |
| Oxidation stability | 30% $H_2O_2$ 60° C. for 20 hours | 91.23 | NA |

TABLE 9

Photostability and oxidation stability test results for Compound 1a

| | Stability Conditions | Compound 1a Purity % | XRPD |
|---|---|---|---|
| Photostability | Photo stability 1.2 million lux hours exposed | 99.52 | Same as initial |
| | Photo stability 1.2 million lux hours unexposed | 99.70 | Same as initial |
| Oxidation stability | 30% $H_2O_2$ 25° C. for 3 hours | 99.50 | NA |
| | 30% $H_2O_2$ 25° C. for 24 hours | 94.30 | NA |

As can be seen in Table 9 above, it could be found, even when Compound 1a was exposed to 1.2 million lux hours of ultraviolet and visible light, there was no significant change in the purity and physical properties, indicating that Compound 1a had excellent photostability. In addition, the decomposition of Compound 1a was observed after 24 hours even under oxidative stress conditions. However, as can be seen in Table 8, when the hydrochloride salt of Compound 1 was exposed to 1.2 million lux hours of ultraviolet and visible light, some changes in the purity were observed, and under oxidative stress conditions, Compound 1 showed a decomposition rate of about 8% or more after 20 hours. Therefore, it could be found that Compound 1a had relatively excellent photostability and oxidation stability compared to the hydrochloride salt of Compound 1.

In conclusion, it could be found that the hemifumarate salt of 2-amino-2-(2-(1-decyl-1H-1,2,3-triazol-4-yl)ethyl)propane-1,3-diol (Compound 1) showed excellent effects in terms of low hygroscopicity, standard stock solution stability, photostability, oxidation stability, pH-dependent stability, solubility, and the like compared to the hydrochloride salt and other salts of Compound 1, and had the best physical properties even when evaluated based on solid-state properties (crystallinity, melting point, and low hygroscopicity).

In addition, it was found that Compound 1a according to the present invention is a salt satisfying all of the following requirements: 1) low-hygroscopicity requirement of less than 2% water absorption rate at 90% RH in DVS, which is a minimum condition for mass production and storage for clinical use; and standard stock solution stability requirement of more than 2 weeks under high-humidity (40°

C./75% RH, etc.) conditions, and solubility requirement of more than 2 mg/mL in all aqueous media, which is a minimum condition for smooth progress of clinical trials.

In addition, it was found that Compound 1b according to the present invention is a salt showing physical and chemical properties generally similar to those of Compound 1a, with only a slight difference in water absorption rate.

Experimental Example 4: Evaluation of Inhibitory Effect of Compound 1a Against Mouse Immune Cells Fingolimod (FTY720) is a therapeutic drug for multiple sclerosis with a mechanism of action that reversibly captures some of the lymphocytes in the lymph nodes or bone marrow, sequestering the lymphocytes in secondary lymphoid organs and inhibiting their entry into the central nervous system, or reduces the number of lymphocytes circulating in blood, reducing the number of activated lymphocytes that reach the brain.

In order to examine whether Compound 1, which acts on the S1P receptor, also is effective in reducing lymphocytes, the effect of Compound 1 on immune cells was evaluated. After oral administration of Compound 1 to mice at 3 mg/kg/day, changes in lymphocytes in peripheral blood (PB) and bone marrow (BM) were classified into T cells, CD4 T cells, and CD8 T cells. FACS analysis was performed 0, 4, 8, 12, 24, and 36 hours after administration of the test substance. Cell number was measured and expressed as a percentage relative to that at time 0 (% of control).

Figure 4:
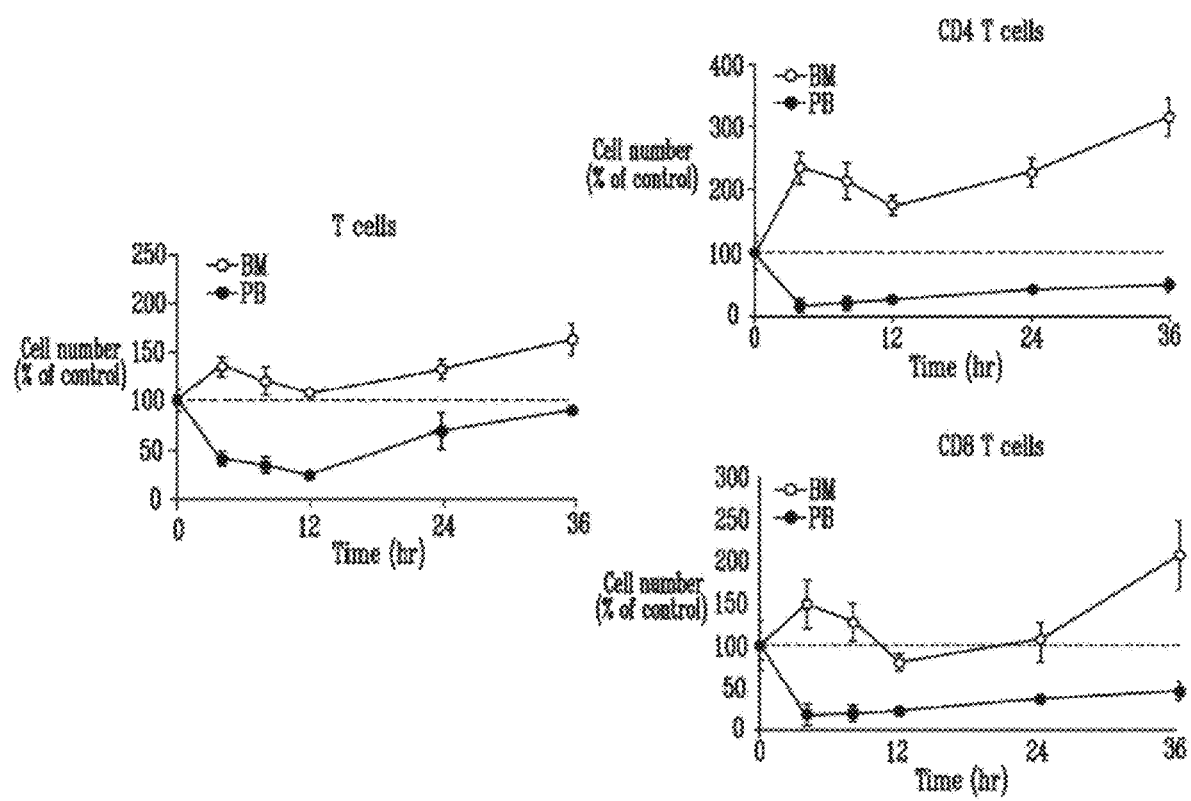
FIG. 4 depicts graphs showing changes in the number of total T cells and T cell subtypes in mice after oral administration of Compound 1a (3 mg/kg/day).

Referring to FIG. 4, it could be found that, by administration of 3 mg/kg of Compound 1a, T cells, CD4 T cells, and CD8 T cells in peripheral blood were all decreased starting from 4 hours to 40.6%/41.6%, 16.4%/17.6%, and 5.9%/9.3%, respectively, relative to those at time 0. The decrease was maintained until 12 hours, and then the cell number was restored to 88.9% at 36 hours. Dose dependence appeared in T cells at 24 hours after administration, and in the case of CD4 T cells and CD8 T cells, a dose-dependent decrease in the cell number could be observed from 4 to 24 hours after administration.

In bone marrow (BM), a T-cell distribution of 135%/120% at 4 hours after administration of 3 mg/kg of Compound 1a and 131%/118% at 24 hours after administration could be observed. This is believed to be because receptor internalization occurred due to Compound 1 and T cell release was suppressed.

It could be found that, after administration of 3 mg/kg of Compound 1a, the cell number of T cells decreased starting from 4 hours, and the inhibitory effect of Compound 1a was maintained to some extent until 24 hours and then the cell number was restored. In conclusion, it could be found that administration of Compound 1a decreased the number of lymphocytes circulating in blood, thereby exhibiting an immunosuppressive effect.

Experimental Example 5: Evaluation of Inhibitory Effect of Compound 1a Against Rat Immune Cells In order to evaluate the effect of Compound 1a on rat immune cells, Compound 1a was administered orally to SD rats at 10 mg/kg/day, and then lymphocytes in peripheral blood (PB) and bone marrow (BM) were classified into T cells, CD4 T cells, and CD8 T cells. FACS analysis was performed 0, 4, 8, 12, 24, 36, and 48 hours after administration of the test substance. Cell number was measured and expressed as a percentage relative to that at time 0 (% of control). The numbers of T cells, CD4 T cells, and CD8 T cells were measured and expressed as percentages relative to those at time 0 (% of control).

Figure 5:
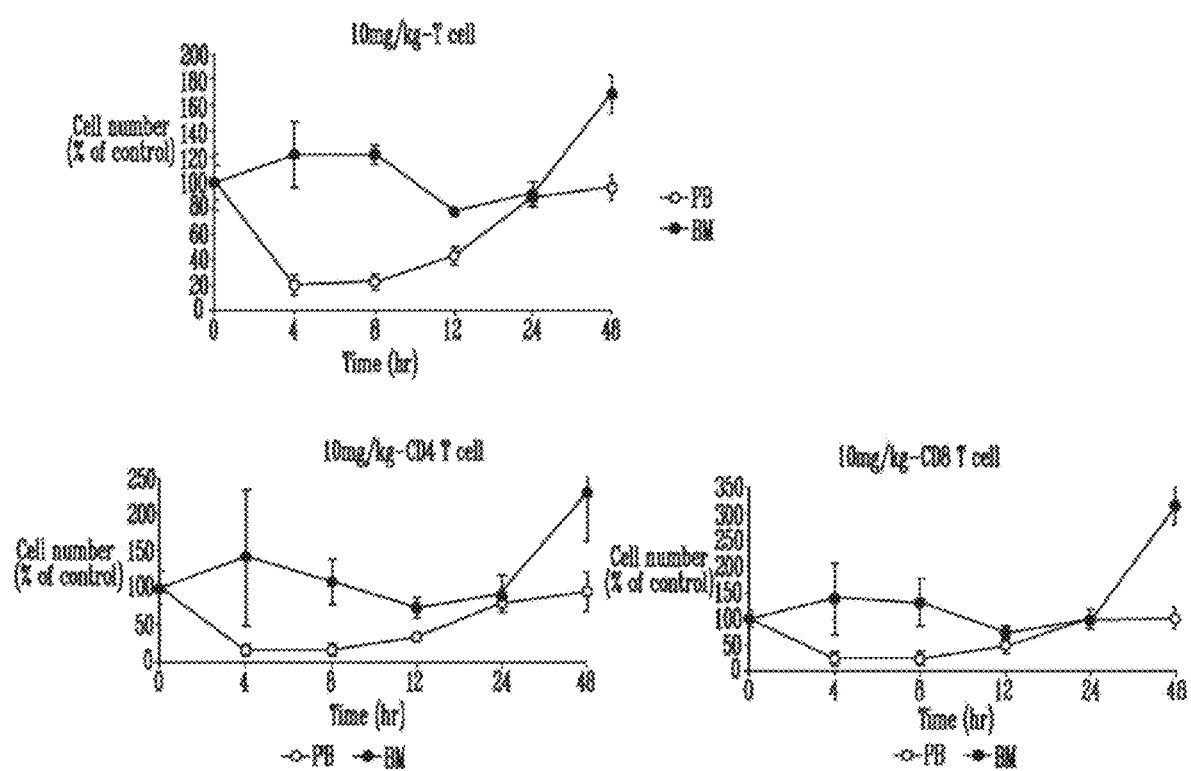
FIG. 5 depicts graphs showing changes in the number of total T cells and T cell subtypes in rats after oral administration of Compound 1a (10 mg/kg/day).

Referring to FIG. 5, it could be found that the number of T cells decreased in peripheral blood (PB) starting from 4 hours after administration of Compound 1a. It could be found that the inhibitory effect was dose-dependent (70%, 80%, and 87%), and the inhibitory effect was maintained until 24 hours after administration of 110 mg/kg of the compound. On the contrary, it could be found that, in bone marrow (BM), there was no change or a tendency to increase.

Through this study, it could be found that Compound 1a exhibited an immunosuppressive effect by reducing the number of lymphocytes in peripheral blood (PB) after oral administration. In addition, it could be found that, in bone marrow (BM), there was no change or a tendency to increase. This effect is believed to be related to the mechanism by which Compound 1 acts as a functional antagonist on the S1P receptor present in lymph nodes, bone marrow (BM), etc., thereby inhibiting lymphocyte.

Experimental Example 6: Evaluation of Inhibitory Effect Against Inflammatory Bowel Disease Using DSS-Induced Mouse Model The effectiveness of Compound 1a against inflammatory bowel disease was evaluated using the dextran sulfate sodium (DSS)-induced colitis model. In the mouse model, inflammatory bowel disease was induced by administering DSS to mice at a concentration of 2.5% via drinking water. Mice were divided into a test group administered Compound 1a, a positive control group administered ozanimod or MTX (methotrexate), a vehicle group, and a normal control group, and each group had n=10. Compound 1, a compound of the present invention, was orally administered at doses of 5 and 10 mg/kg once a day for 7 days to the inflammatory bowel disease-induced model, and ozanimod as a positive control was administered orally at a dose of 5 mg/kg once a day, and MTX (methotrexate) as a positive control was administered intraperitoneally at a dose of 3 mg/kg three times a week.

FIG. 6 shows the disease activity index (DAI) of DSS-induced colitis mice and the area under curve (AUC) of the disease activity index of the DSS-induced colitis mice. DAI represents the total score of weight loss relative to initial weight, stool consistency, and degree of intestinal bleeding of the mouse. The criteria for calculation of DAI are shown in Table 10 below, and DAI was evaluated on days 0, 1, 2, 3, 4, 5, 6, 7, and 8.

TABLE 10

| Score | Weight loss relative to initial weight | Stool consistency | Intestinal bleeding |
|---|---|---|---|
| 0 | <1% | Normal | Occult blood not detected (negative hemoccult) |
| 1 | 1-5% | Soft but still formed | Occult blood detected (low luminol intensity) |
| 2 | 6-10% | Soft | Occult blood detected (high luminol intensity) |
| 3 | 11-18% | Very soft (wet) | Visual detection of blood stain in stool |
| 4 | >18% | Watery diarrhea | Intestinal bleeding |

Referring to FIG. 6, it could be found that the disease activity index statistically significantly decreased in all of the group administered 3 mg/kg of the positive control MTX, the group administered 5 mg/kg of ozanimod, the group administered 5 mg/kg of Compound 1, and the group administered 10 mg/kg of Compound 1, compared to the negative control group (vehicle).

In particular, as a result of administering 5 mg/kg of Compound 1a and 10 mg/kg of Compound 1a, it could be found that clinical indicators according to weight loss, stool consistency, and degree of intestinal bleeding were equivalent to or higher than those of ozanimod, which has been previously used as a targeted therapeutic agent for ulcerative colitis.

For the above evaluation results, statistical analysis was performed between the negative control group and the test groups or between the two test groups, and for comparison between the groups, Student's t-test or Mann Whitney U test was performed and showed a significant difference (p-value: 0.05 or less).

Thereby, it could be confirmed that Compound 1a is a substance having an inhibitory effect on inflammatory bowel disease.

Experimental Example 7: Evaluation of Effect of Compound 1a on Cardiovascular System 1) Evaluation of Effect of Compound 1a on HEK293 Cells Overexpressing hERG Gene The effect of Compound 1a on hERG channel currents was evaluated by applying Compound 1a to HEK-293 cells that stably expressed the hERG potassium ion channel as a result of introducing hERG (human Ether-a-go-go Related Gene) thereinto. Compound 1a was set at concentrations of 1, 3, 10, and 30 µM. In addition, on each experimental day, a random cell for which hERG channel currents for a negative control substance or each concentration of a test substance had been recorded was treated.

Referring to FIG. 7, it was shown that the compensated suppression rates (%) of hERG channel currents by Compound 1 at concentrations of 1, 3, 10, and 30 µM (groups B to E) were 9.94±1.96, 13.98±4.48, 35.03±12.09 and 82.62±7.31% (n=3), respectively, and the compensated suppression rate (%) of hERG channel currents in the negative control group (group A) was 0±4.12 (n=3). That is, it could be found that NCX736 (groups D and E) at concentrations of 10 and 30 µM showed a statistically significant difference compared to the negative control group (group A).

The cells were treated with E-4031 at a concentration of 0.1 µM used as a positive control (group F) under the same conditions as above. The compensated suppression rate (%) of hERG channel currents in group F showed a high value of 92.64±1.66% (n=5). From these results, this test method is considered to be a suitable method for evaluating the effect of Compound 1 on hERG channel currents.

In the evaluation of the effect on hERG channel currents using the hERG gene-introduced HEK-293 cells under the above conditions, as a result of treating the cells with the test substance Compound 1a at a concentration of up to 30 µM, the compensated suppression rate (%) of hERG channel currents was shown to be 82.62±7.31%, and the half-maximum inhibitory concentration (IC50) against the K$^+$ ion channels was calculated to be 12.94 µM (Hill coefficient: 1.527). Therefore, it could be found that Compound 1a is a substance that does not inhibit hERG potassium channel activity and does not cause cardiac abnormalities.

2) Evaluation of Effect on Cardiovascular System Using Beagle Dogs

Compound 1a was orally administered to four non-anesthetized and unrestrained male beagle dogs implanted with remote transmitters. Next, the heart rates of the four beagle dogs were measured to evaluate the effect of Compound 1a on the cardiovascular system, and whether abnormal symptoms occurred was visually checked.

In this experiment, the test substance was administered to each of the four beagle dogs in four steps. In the first administration step (0 mg/kg of Compound 1a), 0.5% MC aqueous solution as control vehicle was administered, and in the second administration step, 12.5 mg/kg of Compound 1a was administered. In the third administration step, 25 mg/kg of Compound 1a was administered, and in the fourth administration step, 50 mg/kg of Compound 1a was administered. The first to fourth administrations were performed at one-week intervals. Additionally, 0 hour before administration of the test substance, and 0.5 hours, 1 hour, 2 hours, 3 hours, 4 hours, 6 hours, 8 hours, 12 hours, and 24 hours after administration of the test substance, the heart rates of the beagle dogs were measured.

Figure 8:
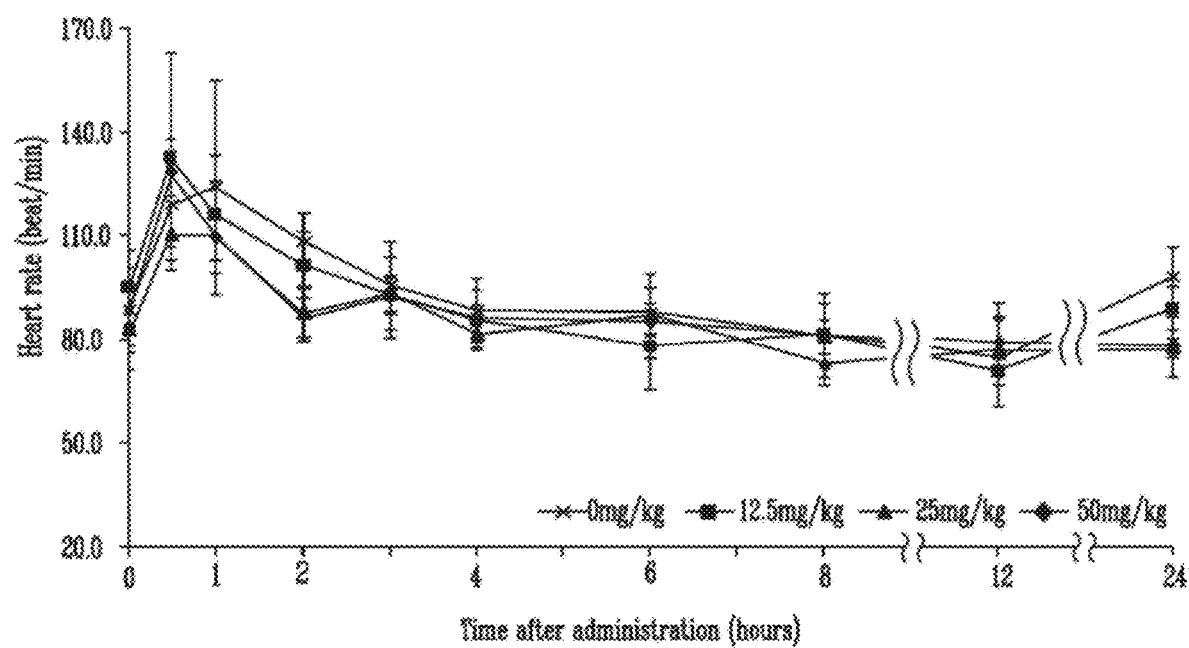
FIG. 8 is a graph showing the results of measuring the heart rate of beagle dogs after oral administration of Compound 1a (12.5, 25, and 50 mg/kg).

Referring to FIG. 8, it could be found that there was no change in the heart rate even when Compound 1a was administered at doses of 12.5, 25, and 50 mg/kg.

In addition, as a result of visually observing general symptoms in the beagle dogs, no abnormal symptoms were observed when Compound 1a was administered at doses of 12.5, 25, and 50 mg/kg.

As described above, from the results of evaluating the inflammatory bowel disease inhibitory effect using the DSS-induced mouse model and the results of measuring the heart rates of the beagle dogs administered Compound 1a and visually checking whether abnormal symptoms occurred, it could be found that a pharmaceutical composition, as an active ingredient, containing the compound represented by Formula 1, an optical isomer thereof, or a pharmaceutically acceptable salt thereof according to the present invention, is effective in preventing or treating inflammatory bowel disease by acting as a functional antagonist for S1PR1 and S1PR4. In addition, it could be found that the pharmaceutical composition according to the present invention acts as a functional antagonist for S1PR1 and S1PR4 among S1P receptor subtypes (S1P1, S1P2, S1P3, S1P4 and S1P5), thereby exhibiting an effect of preventing or treating inflammatory bowel disease without causing cardiovascular disease side effects.

Experimental Example 8: Evaluation of Antifibrotic Effect Using Mouse Kidney Fibrosis Model The antifibrotic effect of Compound 1a in renal disease was evaluated using the unilateral ureteral obstruction (UUO) model, which is a renal fibrotic disease model. Kidney fibrosis was induced by unilateral ureteral obstruction of mice, and then Compound 1a at 10, 30, and 90 mg/kg/day and the positive control substance telmisartan at 30 mg/kg/day were orally administered to the mice once a day for 2 weeks.

Figure 9:
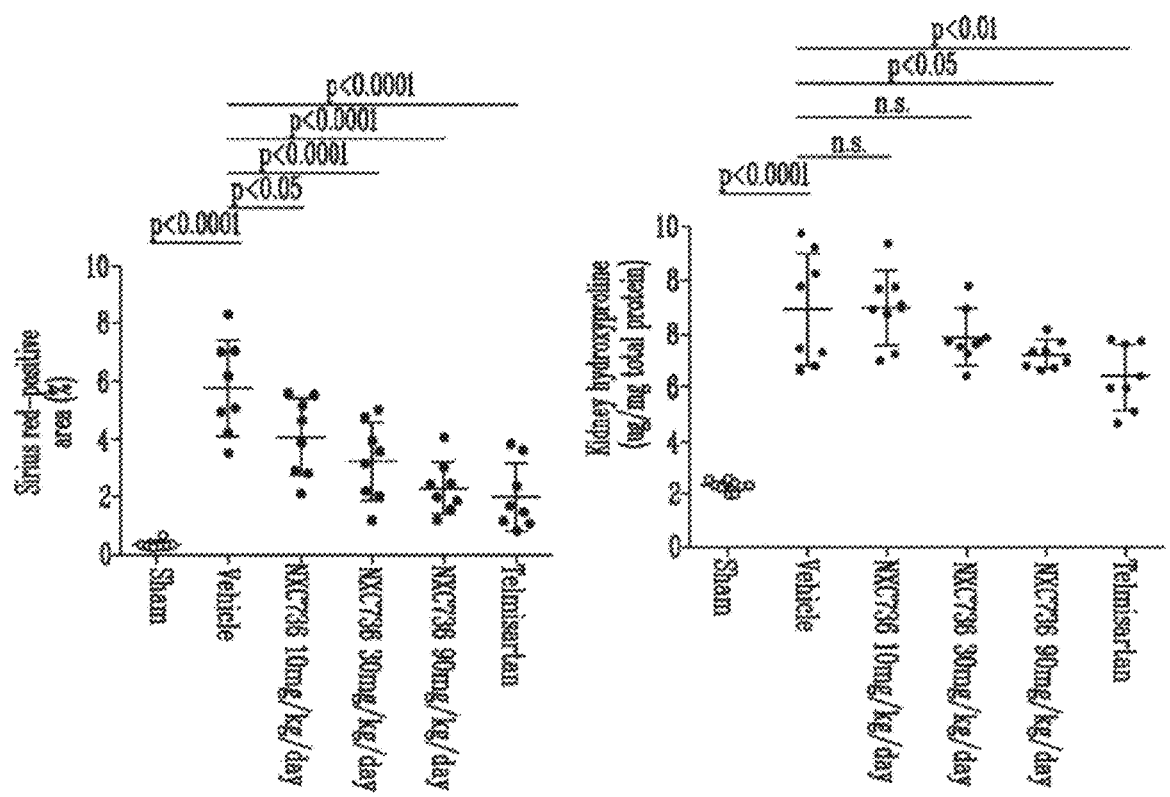
FIG. 9 depicts graphs showing the effect of Compound 1a (10, 30, and 90 mg/kg/day) on renal fibrosis in an UUO mouse model.

Referring to FIG. 9, it could be found that the fibrosis area (Sirius red positive area (%)) and kidney hydroxyproline in the vehicle were significantly increased compared to those in the negative control group (sham), causing renal fibrosis. Telmisartan, used as a positive control substance, statistically significantly reduced kidney hydroxyproline ($p<0.0001$). Kidney hydroxyproline statistically significantly decreased ($p<0.05$, $p<0.01$, $P<0.001$) in all of the groups administered 10, 30, and 90 mg/kg/day of Compound 1a, and in particular, Kidney hydroxyproline statistically significantly decreased ($p<0.05$) in the group administered 90 mg/kg/day of Compound 1a. As a result, it could be found that Compound 1a is a substance with an antifibrotic effect, and that Compound 1a exhibited an inhibitory effect on kidney fibrosis in the UUO-induced mouse renal fibrosis model in a dose-dependent manner.

Experimental Example 9: Evaluation of Antifibrotic Effect Using Adenine-Induced Renal Failure Rat Mouse Model The antifibrotic effect of Compound 1a was evaluated using an adenine-induced chronic kidney disease model. 0.5% adenine (in 0.5% CMC) was orally administered to mice for 4 weeks to induce chronic kidney disease, and Compound 1a at 10, 30, and 90 mg/kg/day and the positive control substance telmisartan 10 mg/kg/day were administered orally to the mice for 3 weeks, followed by measurement of serum creatinine, serum BUN, and kidney hydroxyproline, and histopathology. In addition, the tubular-interstitial index value was determined based on the above measurement results.

Figure 10:
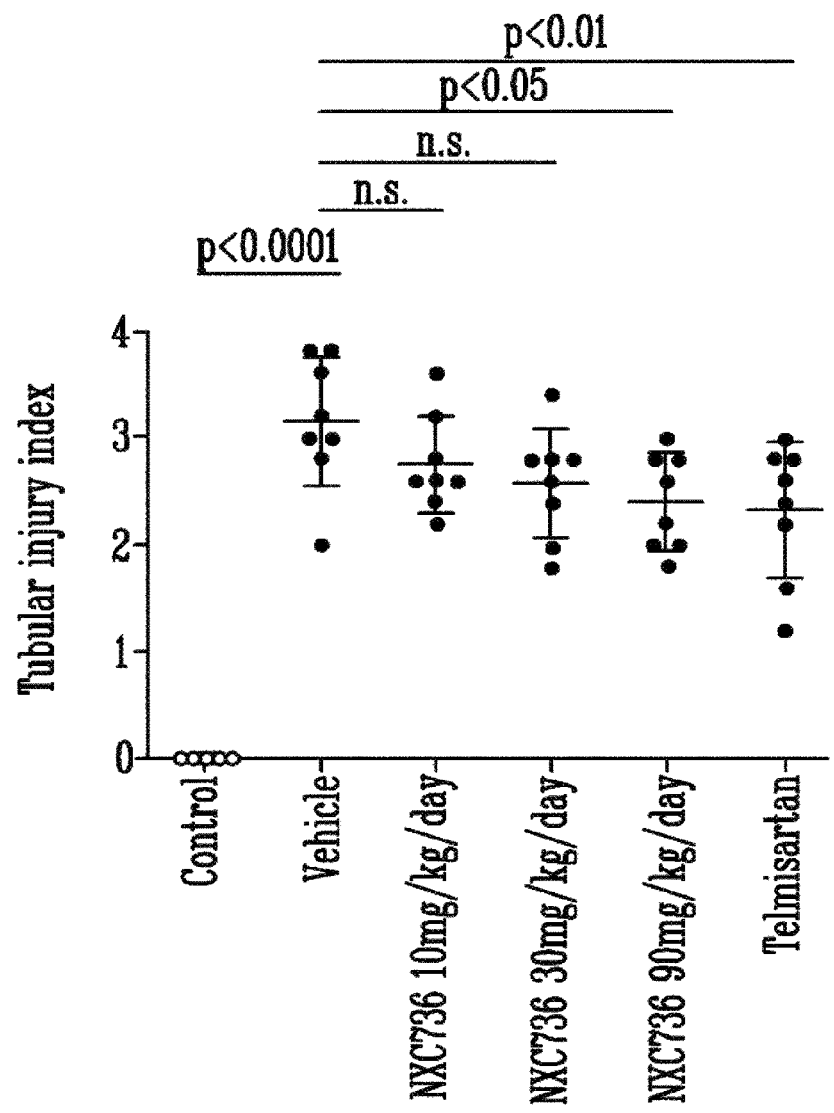
FIG. 10 is a graph showing the effect of Compound 1a (10, 30, and 90 mg/kg/day) on renal fibrosis in an adenine-induced CKD mouse model.

As a result of biochemical analysis, it was shown that, in the adenine-induced CKD model, the vehicle group had a serum creatinine level of 1.15±0.25 (mg/dl) and a serum BUN level of 202.3±32.1 (mg/dl), which significantly increased compared to those of the control group. At 90 mg/kg/day of Compound 1a, the serum creatinine level was 0.90±0.12 mg/dl, which decreased compared to that of the vehicle group, and the serum BUN level was 157.4±32.3 (mg/dl), which decreased compared to that of the vehicle group. The kidney hydroxyproline level in the group administered 30 mg/kg/day of Compound 1a statistically significantly decreased compared to that in the control group. Referring to FIG. 10 showing the tubular-interstitial index, it could be seen that kidney fibrosis statistically significantly decreased in the group administered orally administered Compound 1a at 90 mg/kg/day and the group administered telmisartan. In conclusion, the antifibrotic effect of Compound 1a in the adenine-induced chronic renal fibrosis model could be confirmed.

Experimental Example 10: Evaluation of Alopecia Areata Inhibitory Effect Using Mouse Alopecia Areata Model The efficacy of Compound 1a against alopecia areata was evaluated using a model (C3H/HeJ) with spontaneous alopecia areata. The C3H/HeJ mice used in the test are animals that spontaneously develop alopecia areata with increasing age. Lymph node cells obtained from over 20-week-old C3H/HeJ mice that had spontaneously developed alopecia areata were proliferated and injected into 10-16-week-old C3H/HeJ mice that did not develop alopecia areata to induce alopecia areata. 30 mg/kg of Compound 1a was administered orally to the mice for 12 weeks, and then disease-free ratio and AA lesion area were measured.

It was found that there was no significant difference in body weight between the Compound 1a-administered group and the control group, and alopecia areata was observed late in the Compound 1a-administered group (days when 100% alopecia areata was observed—control group: day 56, and Compound 1a-administered group: day 84). In addition, it could be seen that the alopecia areata area observed in the Compound 1a-adminstered group was statistically significantly smaller than that in the control group. (AA lesion area on day 84-control group: about 80%, and Compound 1a-administered group: about 10%).

For reference, the list of abbreviations used in the present specification is as follows:

TABLE 11

List of abbreviations

| | | | |
|---|---|---|---|
| MeOH | Methanol | THF | Tetrahydrofuran |
| EtOH | Ethanol | 2-MeTHF | 2-methyl tetrahydrofuran |
| IPA | Isopropanol | Et$_2$O | Diethyl ether |
| MEK | Methyl ethyl ketone | MTBE | Methyl t-butyl ether |
| MIBK | Methyl isobutyl ketone | EA | Ethyl acetate |
| MeCN | Acetonitrile | DMA | Dimethyl acetamide |
| DCM | Dichloromethane | Water | Water |
| DSC | Differential scanning calorimetry | RPM | Rotations/revolutions per minute |
| Eqv. | Equivalent | RT | Room temperature |
| min. | Minute(s) | TGA | Thermogravimetric analysis |
| NA | Not applicable | XRPD | X-ray powder diffraction |
| PLM | Polarized light microscopy | w.r.t. | With respect to |
| DVS | Dynamic vapor sorption | HPLC | High performance liquid chromatography |
| CAD | Charged aerosol detector | n-BuOH | n-Butanol |
| NMR | Nuclear magnetic resonance | | |

The invention claimed is:

1. A hemifumarate salt of 2-amino-2-(2-(1-decyl-1H-1,2,3-triazol-4-yl)ethyl)propane-1,3-diol, which is a compound represented by Formula 1a below:

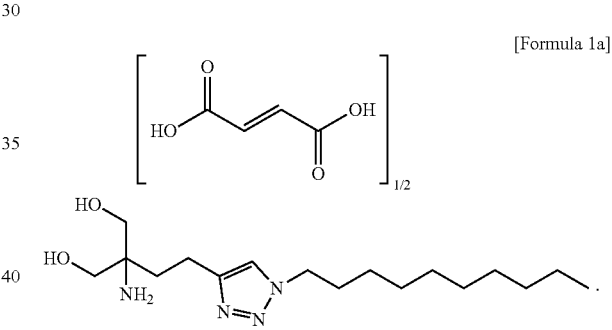

[Formula 1a]

2. The hemifumarate salt according to claim 1, wherein the salt is in crystalline form.

3. The hemifumarate salt according to claim 2, which shows an X-ray power diffraction (XRPD) pattern comprising 2θ values of 6.3±0.2°, 9.4±0.2°, 18.5±0.2°, 19.0±0.2°, 19.9±0.2°, 20.7±0.2°, 25.5±0.2°, 28.7±0.2°, and 29.0±0.2°.

4. The hemifumarate salt according to claim 1, which shows a water adsorption rate of less than 2% under 90% RH conditions in DVS.

5. The hemifumarate salt according to claim 1, which has a melting endothermic onset temperature of about 82° C. in differential scanning calorimetry (DSC).

6. A method of treating multiple sclerosis, ischemic stroke, focal segmental glomerulosclerosis (FSGS), interstitial fibrosis and tubular atrophy (IFTA), inflammatory bowel disease, or alopecia areata (AA), comprising administering to a subject a pharmaceutically effective amount of the hemifumarate salt of 2-amino-2-(2-(1-decyl-1H-1,2,3-triazol-4-yl)ethyl)propane-1,3-diol according to claim 1.

7. The method according to claim 6, wherein the method treats inflammatory bowel disease by specifically binding S1PR1 and S1PR4 receptors, and wherein inflammatory bowel disease is ulcerative colitis (UC) or Crohn's disease (CD).

8. The method according to claim 6, wherein the method does not cause cardiovascular disease side effects.

* * * * *